Figure 1:
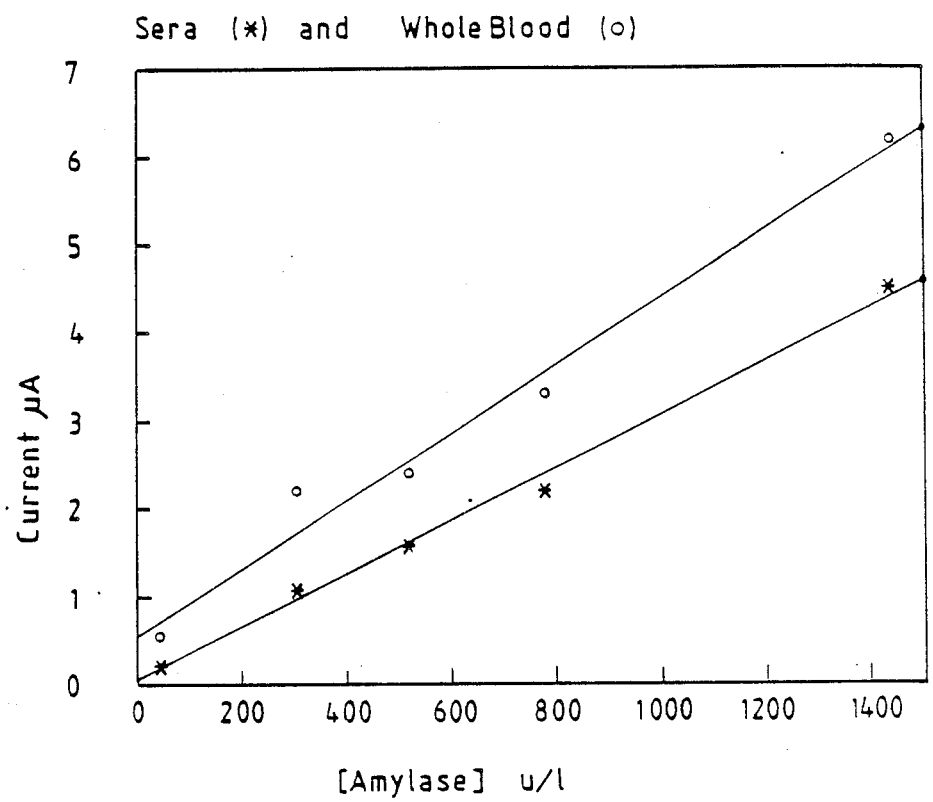

United States Patent [19]

Batchelor et al.

[11] Patent Number: 4,912,041
[45] Date of Patent: Mar. 27, 1990

[54] DETERMINATION OF AMYLASE

[75] Inventors: Mark J. Batchelor, Reading; Stephen C. Williams, Abingdon; Mokina J. Green, Buckinghamshire, all of Great Britain

[73] Assignee: Medisense, Inc., Cambridge, Mass.

[21] Appl. No.: 247,780

[22] Filed: Sep. 21, 1988

[30] Foreign Application Priority Data

Sep. 22, 1987 [GB] United Kingdom ............. 8722278

[51] Int. Cl.$^4$ .................. C12P 19/04; C12Q 1/26; C07H 5/04
[52] U.S. Cl. ...................... 435/101; 435/25; 435/810; 435/99; 435/22; 536/18.7; 536/14.2
[58] Field of Search ............ 435/101, 25, 810; 536/18.7

[56] References Cited

U.S. PATENT DOCUMENTS 4,649,108 3/1987 Blair ........................... 435/14
4,681,841 7/1987 Matsumoto et al. .......... 435/25
4,774,192 9/1988 Terminiello et al. .......... 435/11
4,794,078 12/1988 Blair ........................... 435/810

Primary Examiner—Ronald W. Griffin
Assistant Examiner—Pamela S. Webber

[57] ABSTRACT

A method of assay for the presence of α-amylase in a sample employs a derivatized α-oligosaccharide which can be hydrolyzed by an enzyme mix including α-amylase to yield an electroactive compound, and at least one other enzyme which with α-amylase gives an enzyme mix capable of hydrolyzing the derivatized α-oligosaccharide. The sample is contacted with the derivatized α-oligosaccharide and with the other enzyme to permit hydrolysis of the derivatized α-oligosaccharide and to allow formation of the electroactive compound. An electrode is poised at a potential at which the derivatized α-oligosaccharide is not electrochemically active, the potential being one at which the electroactive compound is electrochemically active. Any current arising from electrochemical activity of the electroactive compound is detected.

9 Claims, 1 Drawing Sheet

DETERMINATION OF AMYLASE

BACKGROUND OF THE INVENTION

The present invention relates to the determination of amylase.

α-Amylase (1,4-α-D-glucan glucanohydrolase, EC 3.2.1.1) catalyses the random endohydrolysis of 1,4-α-glucosidic linkages in starch, glycogen and other α-glucose polymers. It is secreted by the pancreas into the digestive tract where it is involved in the hydrolytic breakdown of food polysaccharides ultimately to produce glucose.

The determination of α-amylase is important in the diagnosis of acute and chronic pancreatitis. These disorders are commonly caused by alcohol abuse or biliary tract diseases. Typically, plasma amylase levels increase five-fold or more over basal levels.

Known methods for amylase determination include amyloclastic, saccharogenic, and chromogenic methods. The amyloclastic methods measure the breakdown of a starch substrate by viscosimetric, turbidimetric iodometric, or nephelometric procedures. They are not frequently used.

The saccharogenic methods measure the formation of sugars by their reducing ability or by specific enzymic methods. The latter include colorimetric and spectrophotometric coupled-enzyme methods involving the measurement of specific chromophores. Many saccharogenic methods suffer from the drawback of having starch as substrate, which does not give reproducible results.

In the chromogenic methods, synthetic substrates are used which yield coloured products that can be measured spectrophotometrically. Their simplicity, sensitivity, suitability for continuous monitoring and convenient automation account for their current popularity.

Examples of chromogenic substrates include dyes covalently attached to an insoluble polysaccharide backbone. The action of the amylase releases soluble dye fragments which can be measured spectrophotometrically after removing unhydrolysed substrate. A disadvantage of this approach is the difficulty in adapting the determination to automatic analysers.

Other chromogenic substrates include p-nitrophenyl oligosaccharides, for example of the general formula PNP-Gn, where PNP represents a p-nitrophenyl group. G represents a glucose residue, and is from 5 to 7. PNP-G5, PNP-G6 and PNP-G7 have all been used in commercial reagents and have become increasingly popular in clinical practice (see, for example, U.S. Pat. No. 4,233,403). Hydrolysis of these substrates by the action of amylase yields a mixture of smaller p-nitrophenyl oligosaccharides. Further hydrolytic degradation of these products, catalysed by α-glucosidase releases the coloured p-nitrophenolate anion which may be determined spectrophotometrically at 405 nm.

The use of the p-nitrophenyl oligosaccharides suffers from a number of drawbacks. They are sensitive to pH, temperature and protein concentration, and they have a lag-phase of around 5 minutes before absorbance readings for a kinetic assay may be accumulated. A major problem is that the reagent mixtures are only stable in solution for a short period.

A variation of this type of assay has recently emerged which appears to offer a shorter lag-phase and longer reagent stability in solution, as described in Clin Chem, 33, 524 (1987). The method uses a blocked p-nitrophenyl maltoheptaoside substrate together with two indicator enzymes; glucoamylase to cleave further the amylase reaction products, and a-glucosidase to release p-nitrophenolate. The blocking group (benzylidene) at the non-reducing end of the oligosaccharide renders the substrate resistant to cleavage by glucoamylase (an exoglycosidase) or glucosidase, but not to amylase (an endoglycosidase). This method probably represents one of the better methods available for amylase determination using solution reagents, though it still takes a total of 4 to 5 minutes.

OBJECT OF THIS INVENTION

The present invention is directed to a fundamentally different assay system, based on an electrochemical determination using a dry reagent system.

SUMMARY OF THE INVENTION

Specifically, this invention resides in measurement of the current from the electrochemical activity of an electroactive compound, such as aminophenol, itself produced by the enzymic hydrolysis of a derivatised oligosaccharide. The enzymic hydrolysis is effected by α-amylase, together with α-glucosidase, and liberates from the derivatised oligosaccharide the aminophenol or other electroactive compound for electrochemical determination. The assay employs dry reagents such as a dry strip system to which the sample is added, and therefore the reagents are not exposed to hydrolytic conditions affecting the accuracy of the assay. The need for constant calibration encountered with liquid assay procedures is thus avoided.

PREFERRED EMBODIMENTS

Typically the oligosaccharide has 5, 6 or 7 saccharide groups, especially glucose groups, and is preferably derivatised with an aminophenol group, especially an unsubstituted p-aminophenyl group. The electroactive part is not limited to the example of p-aminophenol. o-aminophenol can also be used, as can substituted derivatives of these compounds. The molecule has to be in the correct configuration for hydrolysis by α-amylase, and thus all the glycoside linkages are in the α configuration.

It can readily be arranged that the electrochemical determination is effected by poising an electrode at a potential at which the substrate is not electrochemically active, and amperometrically monitoring the electrochemical activity of the compound released by the action of α-amylase and α-glucosidase. The electrochemical activity Typically arises from oxidation of the electroactive compound, but as with other amperometric detection methods, alternative forms of electrochemical activity can provide the basis of the present invention, for example involving reduction of an electroactive compound.

The novel α-oligosaccharides employed as α-amylase substrates in the electrochemical determination are part of this invention. The derivatives of aminophenol can be prepared by hydrogenation of the corresponding nitrophenyl derivatives. In this respect, the hydrogenation of p-nitrophenyl β-glucopyranoside (also known as β-D-glucoside p-nitrophenol) to p-aminophenyl β-glucopyranoside (also known as β-D-glucoside p-aminophenol) has been reported in J Electroanal Chem 116 (1980) 11-24. Reference is also made to this article for studies on the electrochemistry of p-aminophenyl β-glucopyranoside.

For catalytic hydrogenation in methanol using platinum dioxide as catalyst to give derivatised α-oligosaccharides of this invention, it was found that the quantity of catalyst for a given amount of p-nitrophenyl oligosaccharide can be important. Low amounts of catalyst often lead to the recovery of a high percentage of starting material, whereas large amounts of catalyst often give low recoveries of desired product contaminated with various unwanted by-products. The optimum quantity was about 10 mg catalyst per 100 mg p-nitrophenyl α-oligosaccharide, which afforded p-aminophenyl α-oligosaccharide in essentially quantitative yield and around 90-95% purity as determined by HPLC.

In a preferred version the electrochemical determination of the present invention relies on the following reaction sequence:

cally such a mixture is applied as a carbon-containing mix on a conductive track of a support, for example in the close proximity of a reference electrode with a second track. In this way, a miniaturised sensor capable of operating upon a small sample of blood bridging the electrode areas may be produced. The mixture is suitably applied by screen printing.

In a particularly preferred embodiment, the present invention provides a dry strip sensor which comprises an elongate, electrically-insulating substrate having a pair of longitudinal, substantially parallel, electrically-conducting tracks thereupon, each track being provided at the same end with means for electrical connection to a read-out means and provided at the other end with an electrode, one of the electrodes being the reference electrode and the other being the working electrode with the reagent mix of at least the derivatised α-oligosaccharide and the α-glucosidase.

More especially, such a sensor is suitably configured

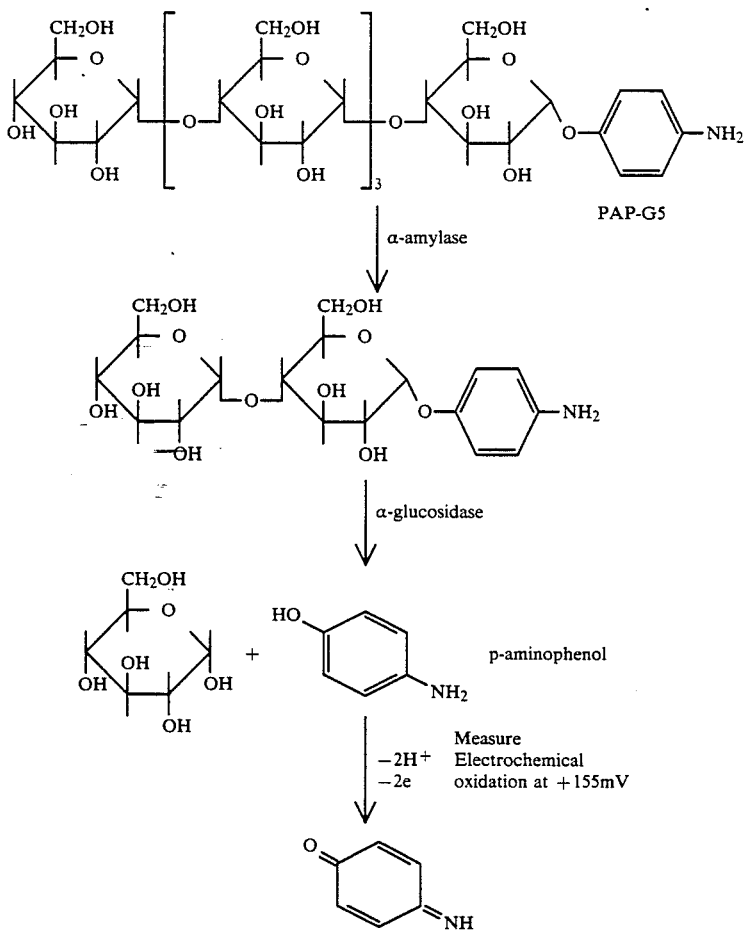

In such a system, the electrochemical measurement of the liberated p-aminophenol is directly proportional to the concentration of amylase in the sample.

The working electrode used for measurement can be of conventional electrode material, and preferably of carbon, for example a glassy carbon or pyrolytic graphite electrode.

In an alternative measurement method of this invention, the working electrode is itself part of a dry strip element, especially a disposable test element. A dry mixture containing the derivatised oligosaccharide and α-glucosidase can be incorporated in the element. Typiin the form of a supporting strip of electrically insulating material such as a synthetic polymer (for instance pvc) carrying at a location between its ends the two electrodes supported on electrically conductive printed tracks. For example, the electrodes can take the form of two rectangular areas side by side on the strip. Such areas can be configured to be covered by a single drop of blood for testing for α-amylase. If desired, non-rectangular electrode areas, for instance diamond-shaped, semicircular, or triangular areas, can be employed to provide a jointly occupied area for optimised contact by a liquid sample.

EXAMPLES OF THE INVENTION

The present invention is illustrated by the following non-limiting Examples. In these Examples, the following abbreviations are employed:
PAP-G5 p-aminophenyl α-maltopentaoside
PAP-G6 p-aminophenyl α-maltohexaoside
PAP-G7 p-aminophenyl α-maltoheptaoside p-Aminophenyl α-Maltohexaoside p-Aminophenyl α-oligosaccharides were prepared by hydrogenation of the corresponding p-nitrophenyl oligosaccharides, and the following procedure is typical. A solution of p-nitrophenyl-α-D-maltohexaoside (170 mg, 0.15 mmol) in dry methanol (10 ml) was stirred at 25° C. with platinum dioxide (17 mg) under an atmosphere of hydrogen for 18 hours. The mixture was filtered and the filtrate concentrated under reduced pressure to afford p-aminophenyl-α-D-maltohexaoside (165 mg, 94% pure by HPLC) as an off-white solid.

Electrode Printing

Working mixes formulated as a smooth thick paste were silk-screen printed onto pre-printed blank electrodes comprising a carbon-tracking layer, silver tracking layer, dielectric layer and Ag/AgCl reference area.

Electrode Testing

A 25 μl sample of analyte was applied to the electrodes so as just to cover the working and reference areas. After a 2 minute incubation period the working electrode was poised at +155mV and an i/t transient recorded, the current at 30 seconds being used as a measure of the p-aminophenol concentration, and hence the α-amylase concentration. The poising potential of +155mV was selected after preliminary studies showed that there was only about a 10% difference across a potential range of +150 to +250mV. While p-aminophenol is oxidised at the potential of +155mV, the p-aminophenyl α-oligosaccharides are not oxidised.

(a) Glucosidase Strips

The initial studies were concerned with investigating the incorporation of α-glucosidase into the working electrode of printed strip electrodes and measurement of the currents obtained on addition of amylase and a p-aminophenol-derivatised substrate.

Substrate Type and Concentration

Glucosidase strips were tested with amylase using three different concentrations of the substrate PAP-G5: 2mM, 4.3 mM and 8.7 mM. Both 4.3 mM and 8.7 mM PAP-G5 gave responses about 20-30% greater than 2 mM PAP-G5. At any given concentration, PAP-G6 was found to give identical responses to PAP-G5 with amylase on glucosidase strips.

Temperature

The responses of glucosidase strips to α-amylase using 4.3 mM PAP-G5 were measured at 37° C. and compared to those obtained at 25° C. Approximately double the current is observed at 37° C.

Incubation Time

A comparison was made between the currents obtained using a 5 minute and a 2 minute incubation period. A 5 minute incubation time gave approximately double the currents seen using a 2 minute period.

(b) Amylase Strips

The incorporation of both the enzyme α-glucosidase and the α-amylase substrate PAP-G6 into the working electrode of printed strips was investigated.

A 2.5 g working mix containing 100 mg PAP-G6 and glucosidase was printed onto blank electrodes. Very high currents were observed when the strips were tested at 37° C. with a 5 minute incubation time.

Substrate Level

Two other levels of PAP-G6 were printed (50 mg and 200 mg each in a 2.5 g mix) and compared to the previously printed strips (100 mg PAP-G6). The glucosidase activity in all three sets of strips was found to be very similar.

The 50 mg level strips behaved very similarly to the 100 mg level, especially at low amylase concentrations, but the higher, 200 mg level strips gave lower currents over the whole range presumably arising from an overloading of substrate on the strip.

Serum

The response of strips (100 mg PAP-G6 in 2.5 g mix) to human serum spiked with α-amylase was determined. The currents obtained were found to be comparable to those using α-amylase in HEPES buffer especially at low amylase levels.

Whole Blood

α-Amylase strips were tested using whole blood spiked with porcine pancreatic amylase. The blood samples were then centrifuged and the sera assayed both on the strips and spectrophotometrically. A comparison of the currents obtained is shown in FIG. 1.

We claim:

1. A method of assay for the presence of α-amylase in a sample, which method comprises
   providing an α-oligosaccharide comprising a hydrolyzable moiety which, when said α-oligosaccharide is hydrolyzed, yields a compound which is electrochemically active at a potential at which said α-oligosaccharide is not electrochemically active;
   providing an enzyme composition which, when mixed and said α-oligosaccharide, will produce said compound from said α-oligosaccharide,
   poising a working electrode at said potential,
   detecting current arising from electrochemical activity of said compound.

2. The method of claim 1, in which said enzyme composition comprises α-glucosidase.

3. The method of claim 2, in which said compound is an aminophenol.

4. The method of claim 3, in which said compound is an unsubstituted p-aminophenol.

5. The method of claim 1, in which said α-oligosaccharide has 5, 6 or 7 glucose groups.

6. The method of claim 1, in which said α-oligosaccharide is selected from the group consisting of p-aminophenyl α-maltopentaoside, p-aminophenyl α-maltohexaoside, and p-aminophenyl α-maltoheptaoside.

7. A method of assaying for α-amylase in a sample, which method comprises the steps of:
   providing a dry-strip disposable test element comprising a substrate carrying two electrodes, one of said electrodes being a working electrode containing a mixture of an α-oligosaccharide and α-glucosidase, said α-oligosaccharide comprising a hydrolyzable moiety which, when said α-oligosaccharide is hydrolyzed, yields an electroactive compound, providing a sensor read-out device to which said electrodes of said dry-strip disposable test element can be electrically connected, said read-out device giving a reading of α-amylase level, electrically connecting said dry-strip disposable test element to said sensor read-out device, applying said sample to said two electrodes of said test element to permit hydrolysis of said α-oligosaccharide and to allow formation of said electroactive compound, poising said electrodes at a potential at which said α-oligosaccharide is not electrochemically active, said potential being one at which said electroactive compound is electrochemically active, detecting any current arising from electrochemical activity of said electroactive compound, and taking a reading from said read-out device indicative of the level of α-amylase in said sample.

8. A dry-strip disposable test element comprising a substrate carrying two electrodes, one of said electrodes being a working electrode containing a mixture of an α-oligosaccharide and α-glucosidase, said α-oligosaccharide comprising a hydrolyzable moiety which, when said α-oligosaccharide is hydrolyzed, yields a compound that is electroactive at a potential at which said α-oligosaccharide is not electroactive, and the other of said electrodes being a reference electrode.

9. A derivatised α-oligosaccharide which is selected from the group consisting of p-aminophenyl α-maltopentaoside, p-aminophenyl α-maltohexaoside, and p-aminophenyl α-maltoheptaoside.

* * * * *

UNITED STATES PATENT AND TRADEMARK OFFICE
CERTIFICATE OF CORRECTION

PATENT NO. : 4,912,041
DATED : March 27, 1990
INVENTOR(S) : Mark J. Batchelor et al.

It is certified that error appears in the above-identified patent and that said Letters Patent is hereby corrected as shown below:

On the title page, item [75] Inventors: change "Mokina J. Green" to read --Monika J. Green--.

Column 2, line 49, "monitoring-the" should be --monitoring the--.

Column 2, line 52, "Typically" should be --typically--.

Column 5, line 6, (two instances) "Examples" should be --examples--.

Signed and Sealed this

Fourteenth Day of July, 1992

Attest:

DOUGLAS B. COMER

*Attesting Officer*  *Acting Commissioner of Patents and Trademarks*